United States Patent
Lund

(10) Patent No.: US 10,779,997 B1
(45) Date of Patent: Sep. 22, 2020

(54) TAMPON INSERTION DEVICE WITH DEPTH INDICATOR

(71) Applicant: Lacey Janell Lund, Rogers, AR (US)

(72) Inventor: Lacey Janell Lund, Rogers, AR (US)

( * ) Notice: Subject to any disclaimer, the term of this patent is extended or adjusted under 35 U.S.C. 154(b) by 0 days.

(21) Appl. No.: 16/746,281

(22) Filed: Jan. 17, 2020

(51) Int. Cl.
*A61F 13/26* (2006.01)
*A61F 13/42* (2006.01)

(52) U.S. Cl.
CPC ............ *A61F 13/266* (2013.01); *A61F 13/42* (2013.01)

(58) Field of Classification Search
CPC .............................. A61F 13/26; A61F 13/266
See application file for complete search history.

(56) References Cited

U.S. PATENT DOCUMENTS

| | | | | |
|---|---|---|---|---|
| 3,042,040 A | * | 7/1962 | Galik ...................... | A61F 13/26 604/15 |
| 4,198,978 A | * | 4/1980 | Nigro ...................... | A61F 13/26 604/14 |
| 4,447,222 A | * | 5/1984 | Sartinoranont ... | A61F 13/55185 604/15 |
| 5,788,663 A | * | 8/1998 | Igaue ...................... | A61F 13/26 604/15 |
| 7,241,274 B2 | * | 7/2007 | Suga ....................... | A61F 13/26 604/11 |
| 7,815,594 B2 | * | 10/2010 | Dougherty, Jr. ........ | A61F 13/26 604/17 |
| 9,387,129 B2 | * | 7/2016 | Bravo .................... | A61F 2/0009 |
| 9,474,656 B2 | * | 10/2016 | Taniguchi ............. | A61F 13/266 |

* cited by examiner

*Primary Examiner* — Catharine L Anderson
(74) *Attorney, Agent, or Firm* — Dale J. Ream

(57) ABSTRACT

A tampon insertion device for inserting a tampon includes a structure for indicating the insertion device is sufficiently inserted into a woman's vagina before deploying the tampon. The tampon insertion device includes a barrel having opposed insertion and proximal end portions and a side wall that defines an interior area therebetween. A tampon is initially positioned in the interior area. A depth indicator having indicia is situated on the side wall of the barrel that is indicative that the barrel is fully inserted, the indicia including one of a recess, a groove, or imprinted matter extending radially about the barrel. The insertion device includes a plunger slidable from a starter configuration extending away from the proximal end portion of the barrel to a deployed configuration positioned downstream inside the interior area. Pressure applied to the plunger causes the plunger to urge the tampon downstream within the interior area.

18 Claims, 6 Drawing Sheets

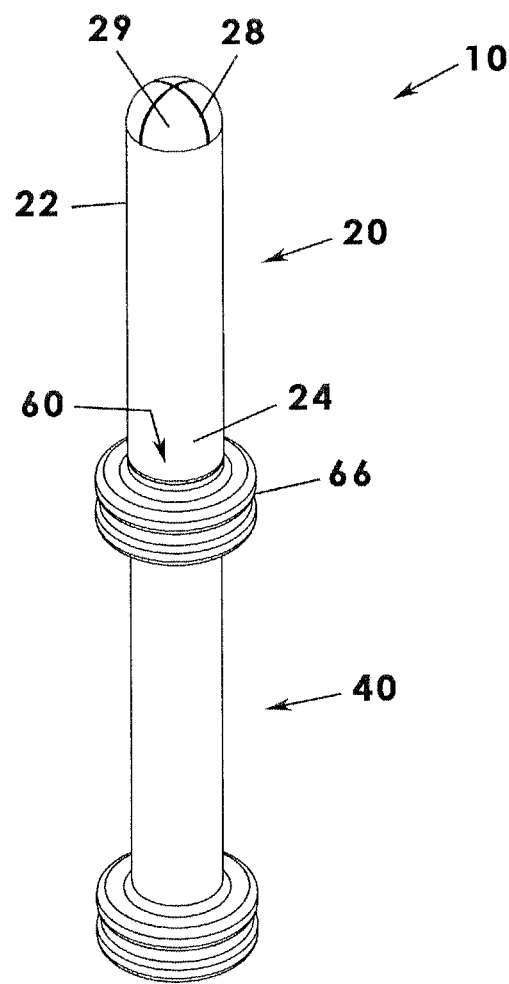
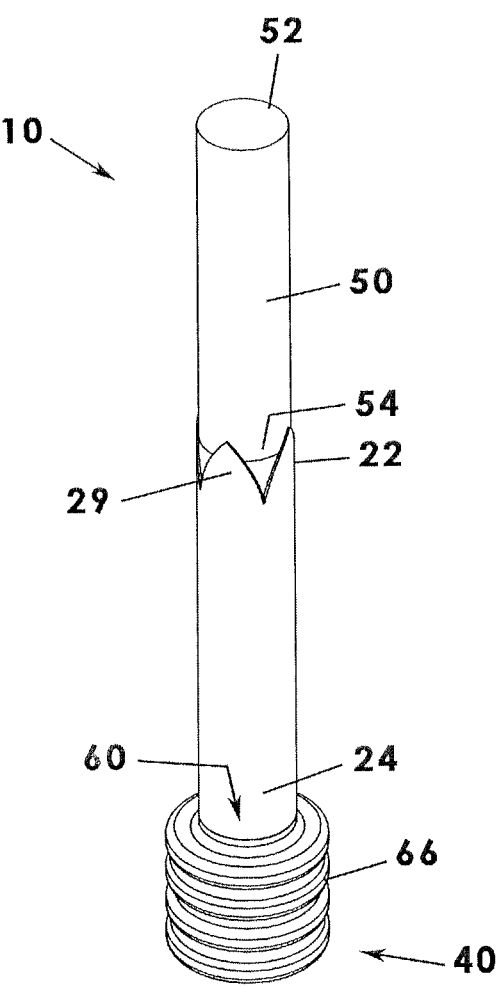
Fig.1a
Fig.1b

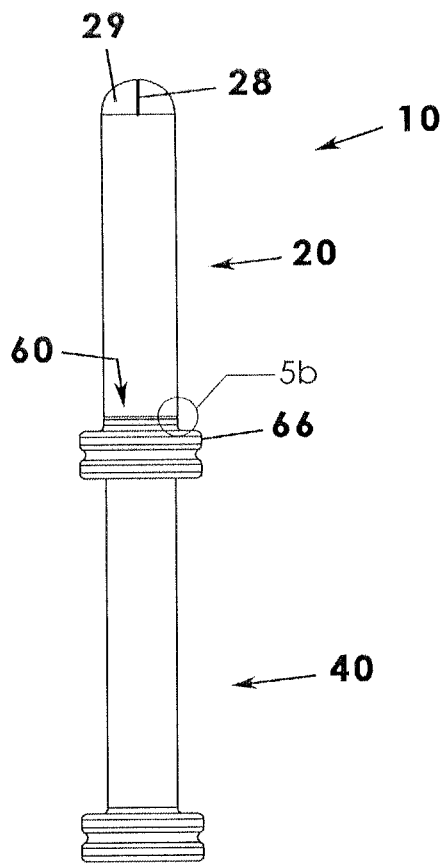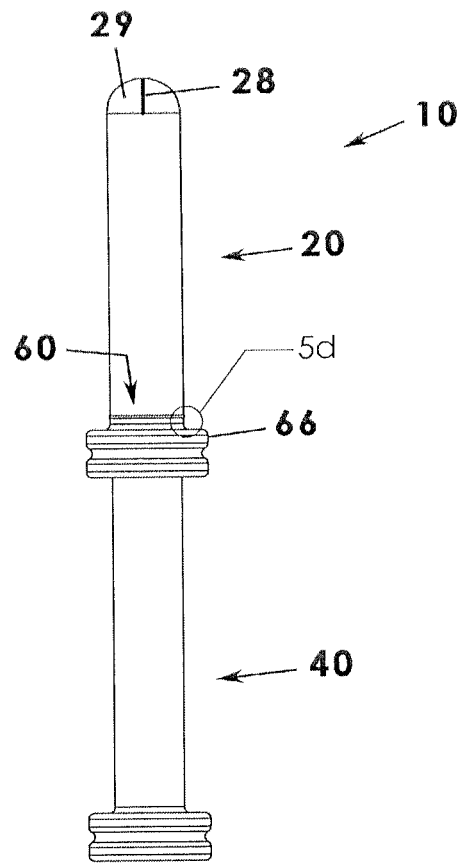
Fig.5a
Fig.5c
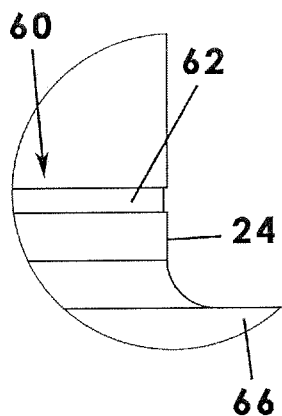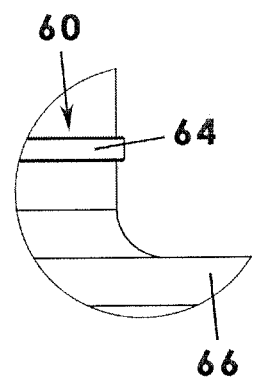
Fig.5b
Fig.5d

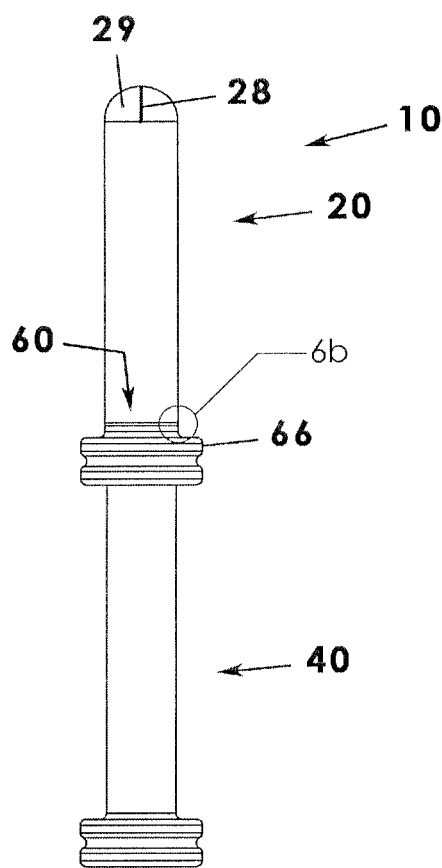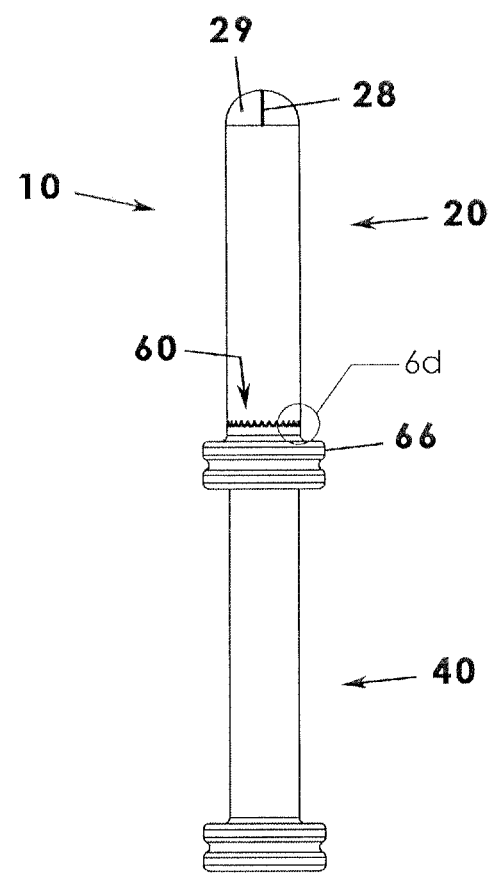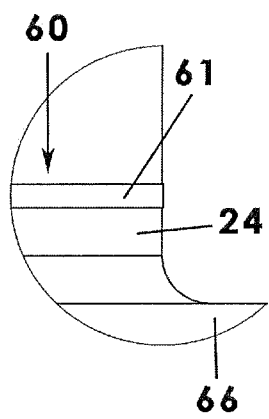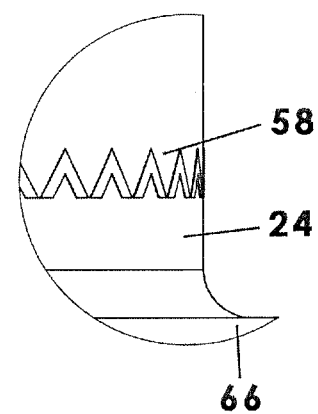
Fig.6a
Fig.6c
Fig.6b
Fig.6d

US 10,779,997 B1

TAMPON INSERTION DEVICE WITH DEPTH INDICATOR

BACKGROUND OF THE INVENTION

This invention relates generally to tampon delivery devices and, more particularly, to an insertion device having indicia indicative of how far the insertion device should be inserted into a user's vagina. In other words, the insertion device includes a visual and tactile indicator of when insertion is sufficiently complete for deployment of a tampon from the insertion device.

A tampon is a feminine hygiene product for insertion into the vagina during menstruation and is designed to absorb the menstrual flow, Once inserted correctly a tampon is held in place by the vagina and expands as it soaks up menstrual blood. Traditionally, a tampon is constructed of cotton and rayon and should be inserted into the deepest portion of the vagina for maximum absorption of blood. The tampon may be "pushed" or positioned using an applicator or handle. In some cases, the tampon may itself be initially contained within an insertion device or barrel that is first inserted into the vagina before the tampon is then forced through an insertion end thereof and is deployed into the vagina.

Although presumably effective for their intended purposes, the traditional construction of a barrel, tampon, and applicator do not indicate to an inexperienced user just how far the barrel and then the tampon should be inserted. More particularly, a teenage girl who is perhaps having her first cycle of menstruation (i.e. her first "period"), may not know when the insertion device is sufficiently inserted into her vagina and, correspondingly, when it is appropriate to deploy the tampon forward of the insertion end.

Therefore, it would be desirable to have a tampon insertion device that includes a depth indicator member having indicia indicative of a depth of insertion so that a tampon may be correctly deployed from an insertion end thereof. Further, it would be desirable to have a tampon insertion device that includes indicia that is tactile or visible to a user.

SUMMARY OF THE INVENTION

A tampon insertion device for inserting a tampon according to the present invention includes a structure for indicating the insertion device is sufficiently inserted into a woman's vagina before deploying the tampon. The tampon insertion devices includes a barrel having an insertion end portion and a proximal end portion opposite the insertion end portion and having a continuous side wall extending therebetween that defines an interior area. A tampon is initially positioned in the interior area of the barrel. A depth indicator member having indicia situated on an outside surface of the continuous side wall of the barrel is indicative that the barrel is fully inserted. The tampon insertion device includes a plunger slidably coupled to the barrel that has a first end engaging a proximal end of the tampon, the plunger having a cylindrical configuration selectively slidable from a starter configuration extending away from the proximal end portion of the barrel to a deployed configuration positioned downstream inside the interior area of the barrel. Pressure applied to the plunger causes the plunger to urge the tampon downstream within the interior area of the barrel.

Therefore, a general object of this invention is to provide a tampon insertion device that includes indicia indicative of a depth of insertion into a vagina so that a tampon may be correctly deployed from an insertion end thereof.

Another object of this invention is to provide a tampon insertion device, as aforesaid, that includes indicia that is tactile or visible to a user.

Still another object of this invention is to provide a tampon insertion device, as aforesaid, having an insertion indicator member positioned adjacent the proximal end that is visible or tactile to a woman while inserting the barrel of the tampon insertion device.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1a is a perspective view of a tampon insertion device having a depth indicator, illustrated in a ready configuration;

FIG. 1b is another perspective view of the tampon insertion device as in FIG. 1a, illustrated in a deployed configuration;

FIG. 2 is an exploded view of the tampon insertion device as in FIG. 1a;

FIG. 3a is a top view of the tampon insertion device as in FIG. 1a;

FIG. 3b is a sectional view taken along line 3b-3b of FIG. 3a;

FIG. 4b is a sectional view taken along line 4b-4b of FIG. 4a;

FIG. 5a is a side view of the tampon insertion device as in FIG. 1;

FIG. 5b is an isolated view on an enlarged scale taken from FIG. 5a, illustrating one variation of the depth indicator member;

FIG. 5c is a side view of the tampon insertion device as in FIG. 1;

FIG. 5d is an isolated view on an enlarged scale taken from FIG. 5c illustrating another variation of the depth indicator member;

FIG. 6a is a side view of the tampon insertion device as in FIG. 1;

FIG. 6b is an isolated view on an enlarged scale taken from FIG. 6a, illustrating another variation of the depth indicator member;

FIG. 6c is a side view of the tampon insertion device as in FIG. 1; and

FIG. 6d is an isolated view on an enlarged scale taken from FIG. 6c illustrating another variation of the depth indicator member.

DESCRIPTION OF THE PREFERRED EMBODIMENT

Figure 2:
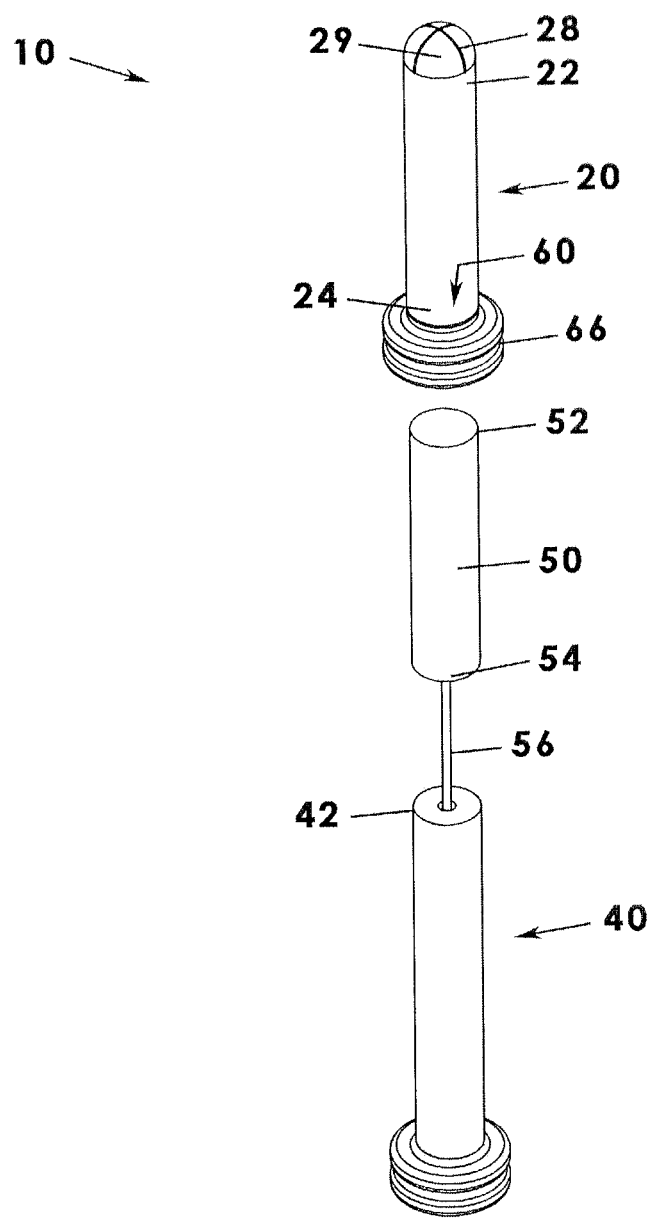
Figure 3A:
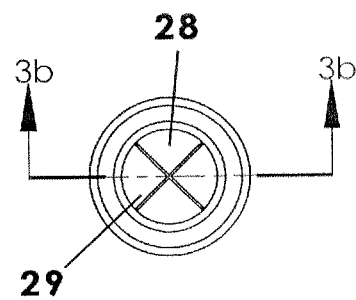
Figure 3B:
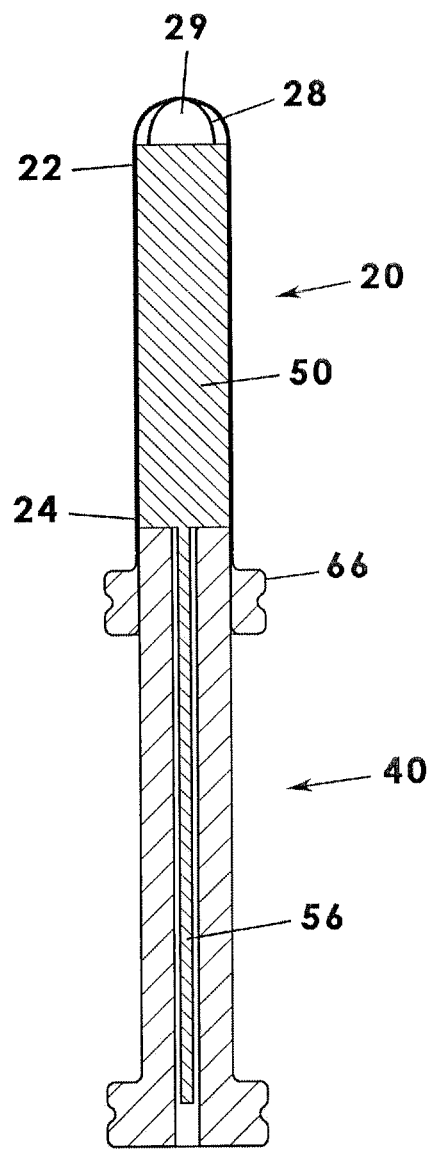

A tampon insertion device having an indicator of a depth of insertion into a vagina according to a preferred embodiment of the present invention will now be described in detail with reference to FIGS. 1a to 6d of the accompanying drawings. The tampon insertion device 10 includes a barrel 20, a tampon 50 initially positioned in the barrel 20, a plunger 40 for pushing the tampon 50 out of the barrel, and a depth indicator member 60 positioned on an outside surface of the barrel 20.

The barrel 20 has an insertion end portion 22 and a proximal end portion 24 opposite the insertion end portion 22, i.e. opposed ends. While the proximal end portion 24 defines an open end, the insertion end portion 22 is initially closed but then opens up as a tampon 50 is pushed out as will be described later. More particularly, a continuous side wall 26 extends between the proximal end portion 24 and the insertion end portion 22, the continuous side wall 26 having a cylindrical configuration that defines an interior area into which other components are situated and some of which move slidably as will be described.

The insertion end portion 22 includes a two or more (also referred to as a plurality) of lines of separation 28 that divides the insertion portion into a plurality of flaps 30 or panels. Initially, the plurality of flaps may have a curved end or domed configuration that limit access to the interior area (FIG. 1) but that separate to form or define an open end when the tampon 50 is pushed downstream and out of the interior area of the barrel 20 (FIG. _), as will be described in more detail below.

Further, the tampon 50 is initially positioned within the interior area of the barrel 20 and is configured to move slidably when pushed or urged downstream by operation of the plunger 40 as explained below. The tampon 50 may be constructed or cotton or a blend of materials suitable to absorb blood and other fluids common to a woman's menstrual period. More particularly, the tampon 50 may have a cylindrical configuration with a flat or truncated distal end 52 (i.e. the upper end). Further, the tampon 50 may include a proximal end 54 opposite the distal end 52 from which a string 56 extends. The string enables a user to extract the tampon 50 more efficiently. In one embodiment, a wax plug (not shown) may be included on the string 56 to absorb blood and to enhance grip.

Figure 4A:
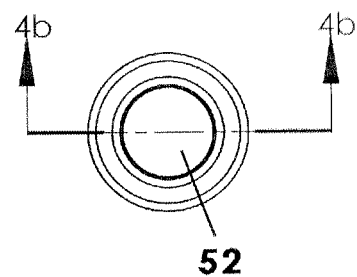
FIG. 4a is a top view of the tampon insertion device as in FIG. 1b.
Figure 4B:
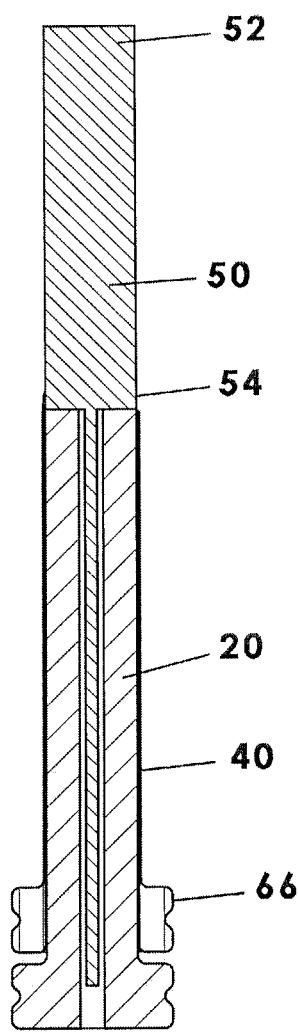

The tampon insertion device 10 includes a plunger 40 configured to move slidably in the barrel 20. More particularly, the plunger 40 may have a tubular or cylindrical configuration that enters the barrel 20 via the proximal end portion 24 and has a first end 42 (i.e. the upper end as illustrated) that engages and bears against a lower end of the tampon 50. The plunger 40 is configured to move downstream toward the insertion end portion 22 when pressure is applied thereto by the hand of a user, downstream movement of the tampon 50. In an embodiment, the plunger 40 may be pushed downstream in the barrel 20 and moves slidably. Continued pressure on the plunger 40 causes the tampon to be pushed out of the insertion end portion 22 (FIG. 4). In some embodiments, the plunger 40 may be threadably linked to the barrel 20 such that a twisting of the plunger 40 results in movement between a starter configuration extending outwardly away from the barrel and a deployed configuration substantially or completely inside the interior area of the barrel 20.

Now, specific attention is given to the depth indicator member 60. A specific and critical object of the present invention is to provide a structure that enables a woman to properly insert and position the tampon insertion device 10 in her vagina before operating the plunger 40 to push the tampon 50 downstream where the tampon 50 will puncture the insertion end and be deployed into an appropriate position in the vagina to be most effective. This feature is critical and non-obvious because a young woman, such as a teenage girl, may be experiencing her first menstrual cycle or may otherwise be inexperienced at inserting a tampon or simply unconfident in doing so.

The inexperienced user may be visually capable of viewing and her vagina and the barrel 20 of the tampon insertion device 10 during insertion thereof. In other instances, however, the girl may be unable to visually see the insertion device but may be able to "feel" the insertion device 10, i.e. the user has tactile perception. The discussion herein may refer to the visual or tactile structure of the depth indicator member 60 as "indicia." The term "indicia" will refer to visual indicia such as a line imprinted in ink, a scale having measurement markings (not shown), a line having a horizontal configuration, a line having a jagged or curved configuration 58, a line having alphanumeric or symbolic characters. Preferably, the indicia extend radially about the cylindrical configuration of the continuous side wall 26 of the barrel 20. Preferably, the depth indicator member 60 extends at least partially around the continuous side wall 26 of the barrel 20. For instance, the depth indicator member 60 may have ring-shaped configuration extending radially about a longitudinal axis defined by the barrel 20. Alternately, the depth indicator member 60 may be a horizontal imprinted line 61 extending horizontally across the side wall of the barrel 20—in other words, perpendicular to the longitudinal extent of the barrel 20.

In some embodiments, the depth indicator member 60 (also referred to merely as indicia) may refer to tactile indicia. More particularly, the depth indicator member 60 may be in the form of a groove 62 recessed into the continuous side wall of the barrel 20, such as in the form of a ring extending completely or at least extending partially radially about the barrel 20 and adjacent to the proximal end portion 24 thereof. In other words, the groove 62 may be a recessed area having a concave configuration perception to the touch. In some embodiments, the depth indicator member 60 may be in the form of a nub 64 extending upwardly from the continuous side wall 26 of the barrel 20, such as in the form of a ring extending completely or at least extending partially radially about the barrel 20 and adjacent to the proximal end portion 24 thereof. In other words, the nub 64 may have a convex and ring-like appearance and perception to the touch. In general, the groove, recessed area, a ring-shaped nub, may be referred to as tactile indicia.

Alternately, the depth indicator member 60 may include a ledge 66 extending outwardly about the proximal end portion 24 of the barrel 20. Part or all of the ledge 66 may include additional or auxiliary visual or tactile indicia indicative the barrel 20 has been sufficiently inserted into the vagina such that the plunger 40 may be operated so as to as deploy the tampon 50 as described above. The distance from the proximal end portion 24 or top of the ledge 66 may be in the range from about 3.5 inches to about 4.0 inches and, preferably, in the range from about 3.7 inches and 3.9 inches. The precise preferred distance is believed to be 3.77 inches.

Importantly, the depth indicator member 60 is positioned or situated adjacent or immediately proximate the proximal end portion 24 of the barrel 20. Positioning the depth indicator member 60 adjacent to the proximal end portion 24 enables a user to see or feel it even when inserting the tampon insertion device 10 into her vagina.

In use, a user inserts the barrel 20 of the tampon insertion device 10 into her vagina until she can see or feel the indicia of the depth indicator member 60—at which time she knows it is appropriate to deploy the tampon 50 inside the interior area defined by barrel 20. Specifically, then, the user may push or rotate the plunger 40 upwardly into the barrel 20 so as to urge the tampon 50 upwardly, i.e. downstream. The tampon 50 is, thus, deployed into the vagina.

It is understood that while certain forms of this invention have been illustrated and described, it is not limited thereto except insofar as such limitations are included in the following claims and allowable functional equivalents thereof.

The invention claimed is:

1. A tampon insertion device with an insertion depth indicator for determining a correct deployment position of a tampon, comprising:
   a barrel having an insertion end portion and a proximal end portion opposite said insertion end portion and having a continuous side wall extending therebetween that defines an interior area;
   a tampon initially positioned in said interior area of said barrel;
   a depth indicia extending at least partially about an outer surface of said continuous side wall as a ring adjacent said proximal end portion of said barrel indicative that said barrel is fully inserted; and
   a ledge fixedly attached to said proximal end portion of said barrel adjacent to said ring and extending outwardly from said continuous side wall, said ledge having an upper surface that is perpendicular to a longitudinal axis defined by said barrel and provides auxiliary indication that said barrel is fully inserted.

2. The tampon insertion device as in claim 1, further comprising:
   a plunger operably coupled to said barrel and having a first end engaging a proximal end of said tampon, said plunger having a cylindrical configuration selectively slidable from a starter configuration extending away from the proximal end portion of the barrel to a deployed configuration positioned inside the barrel;
   wherein pressure applied to said plunger causes said plunger to urge said tampon downstream within said interior area of said barrel.

3. The tampon insertion device as in claim 2, wherein said insertion end portion includes multiple lines of separation configured to separate and define an open end when said plunger is moved toward said deployed configuration.

4. The tampon insertion device as in claim 1, wherein said depth indicia is a groove defined as a ring extending radially about an outer surface of said continuous side wall adjacent said proximal end portion of said barrel.

5. The tampon insertion device as in claim 1, wherein said depth indicia includes a groove defined by an outer surface of said barrel and extending radially, about a portion of said continuous side wall adjacent said proximal end portion of said barrel.

6. The tampon insertion device as in claim 1, wherein said depth indicia includes a tactile member positioned on an outer surface of said continuous side wall of said barrel, said tactile member defining one of a recessed area or a raised surface.

7. The tampon insertion device as in claim 1, wherein said depth indicia includes a line having one of a linear or jagged configuration imprinted on an outer surface of said continuous side wall adjacent said proximal end portion of said barrel.

8. The tampon insertion device as in claim 7, wherein said depth indicia has a ring-shaped configuration that extends at least partially about said outer surface of said continuous side wall.

9. The tampon insertion device as in claim 1, distance between said depth indicia and said insertion end portion is between 3.5 inches and 4 inches.

10. A tampon insertion device for determining a correct position for deployment of a tampon, comprising:
   a barrel having an insertion end portion and a proximal end portion opposite said insertion end portion and having a continuous side wall extending therebetween that defines an interior area;
   a tampon initially positioned in said interior area of said barrel; and
   a depth indicator member having indicia situated on an outside surface of said continuous side wall of said barrel and that is indicative that said barrel is fully inserted;
   wherein said depth indicator member includes a ledge fixedly attached to said proximal end portion of said barrel and extends outwardly from and is perpendicular to said continuous side wall;
   a plunger slidably coupled to said barrel and having a first end engaging a proximal end of said tampon, said plunger having a cylindrical configuration selectively slidable from a starter configuration extending away from the proximal end portion of the barrel to a deployed configuration positioned downstream inside said interior area of said barrel;
   wherein pressure applied to said plunger causes said plunger to urge said tampon downstream within said interior area of said barrel.

11. The tampon insertion device as in claim 10, wherein said insertion end portion includes multiple lines of separation configured to separate and define an open end when said plunger is moved toward said deployed configuration.

12. The tampon insertion device as in claim 10, wherein said depth indicator member is a groove defined as a ring extending radially about an outer surface of said continuous side wall adjacent said proximal end portion of said barrel.

13. The tampon insertion device as in claim 10, wherein said depth indicator member includes a nub extending outwardly as a ring extending at least partially about an outer surface of said continuous side wall adjacent said proximal end portion of said barrel.

14. The tampon insertion device as in claim 10, wherein said depth indicator member includes a tactile member positioned on an outer surface of said continuous side wall of said barrel, said tactile member defining one of a recessed area or a raised surface.

15. The tampon insertion device as in claim 10, wherein said depth indicator member includes a line having one of a linear or jagged configuration imprinted on an outer surface of said continuous side wall adjacent said proximal end portion of said barrel.

16. The tampon insertion device as in claim 15, wherein said depth indicator member has a ring-shaped configuration that extends at least partially about said outer surface of said continuous side wall of said barrel.

17. The tampon insertion device as in claim 10, wherein a distance between said depth indicia and said insertion end portion is between 3.5 inches and 4 inches.

18. The tampon insertion device as in claim 10 wherein said depth indicator includes primary indicia on said continuous side wall proximate said proximal end portion that is indicative that said barrel is fully inserted and an auxiliary indicia immediately adjacent to said primary indicia, said auxiliary indicia including said ledge having at least an upper surface that is perpendicular to said continuous side wall.

* * * * *